United States Patent [19]

Dutcher

[11] 4,155,500
[45] May 22, 1979

[54] DIFFUSER CARTON

[75] Inventor: Daniel P. Dutcher, Woodbury, Minn.

[73] Assignee: Champion International Corporation, Stamford, Conn.

[21] Appl. No.: 901,439

[22] Filed: May 1, 1978

[51] Int. Cl.² .......................... B65D 5/10; B65D 85/00
[52] U.S. Cl. .......................................... 229/8; 229/22; 239/59; 206/45.14
[58] Field of Search .................. 206/0.5, 45.14–45.16, 206/45.19, 476, 491; 229/22, 8; 239/56–57, 59

[56] References Cited

U.S. PATENT DOCUMENTS

| | | | |
|---|---|---|---|
| 1,782,919 | 11/1930 | Feldman | 239/59 |
| 1,900,420 | 3/1933 | Shrader | 229/22 |
| 2,361,923 | 11/1944 | Arneson | 229/22 X |
| 2,738,225 | 3/1956 | Meek | 239/59 |
| 2,894,673 | 7/1959 | Vuillemenot | 229/22 X |
| 3,302,845 | 2/1967 | Gould | 229/22 X |
| 3,610,514 | 10/1971 | Samsing | 229/22 X |
| 3,765,529 | 10/1973 | Mueller | 206/45.14 |
| 3,796,301 | 3/1974 | Arneson et al. | 206/45.14 |
| 3,876,131 | 4/1975 | Tolaas | 229/22 |

*Primary Examiner*—Davis T. Moorhead
*Attorney, Agent, or Firm*—Evelyn M. Sommer

[57] ABSTRACT

A carton constructed from a one-piece, paperboard blank for receiving an air freshener cake has a front panel provided with openings through which the cake material is diffused. The cake is held in clamped relation within the carton by a closure flap foldably connected to the bottom edge of a rear panel which is the mirror-image of the front panel. A slide may be placed in the carton between the front panel and cake. The slide is provided with openings which are moved into and out of registration with the openings of the front panel to open and close the front diffusion panel.

6 Claims, 11 Drawing Figures

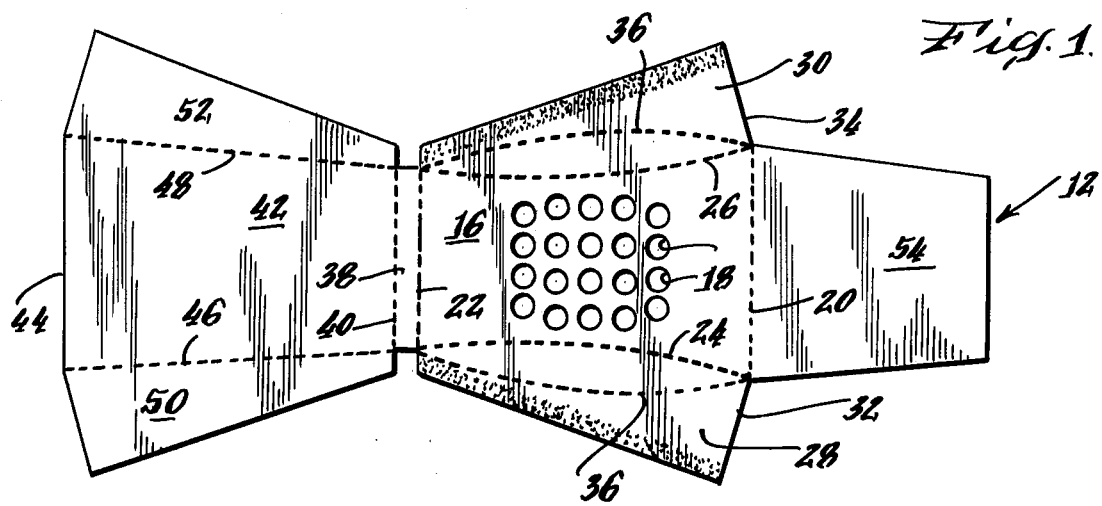
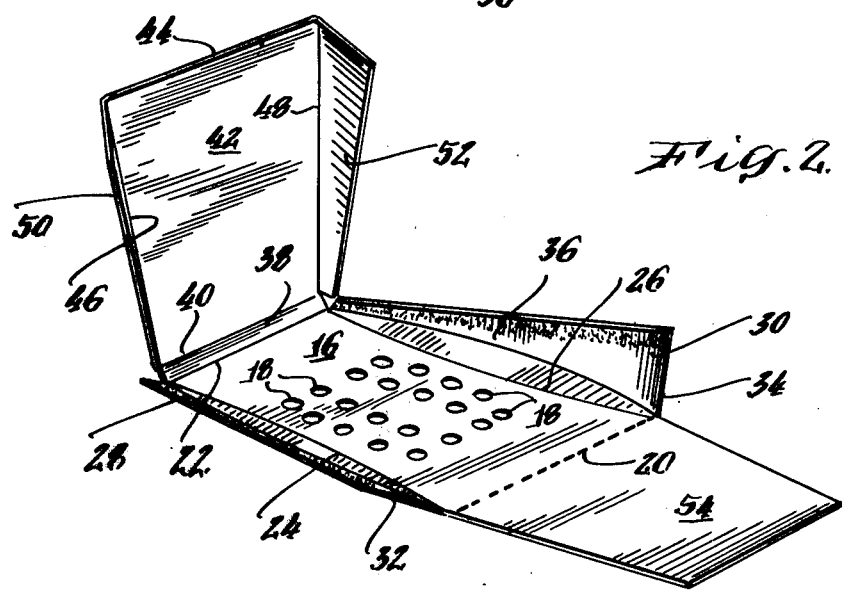
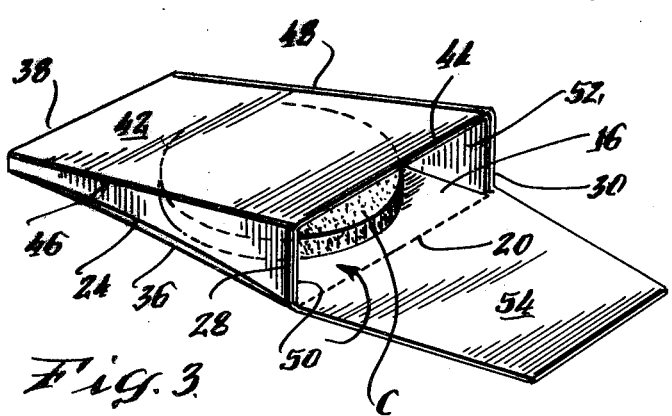
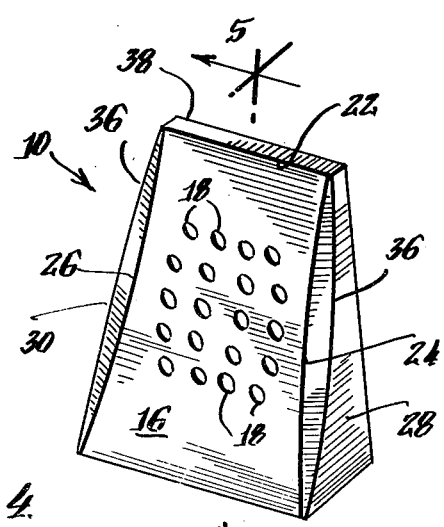

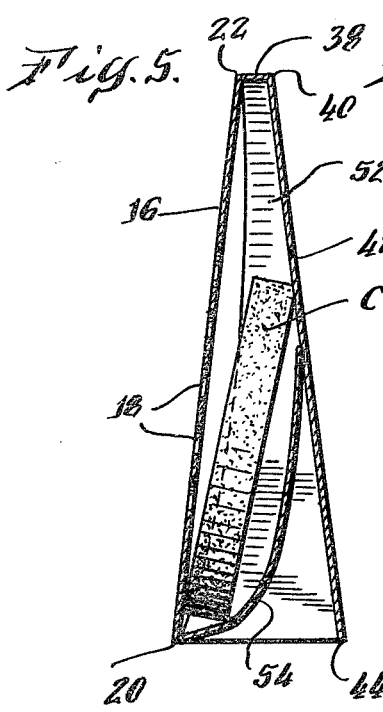
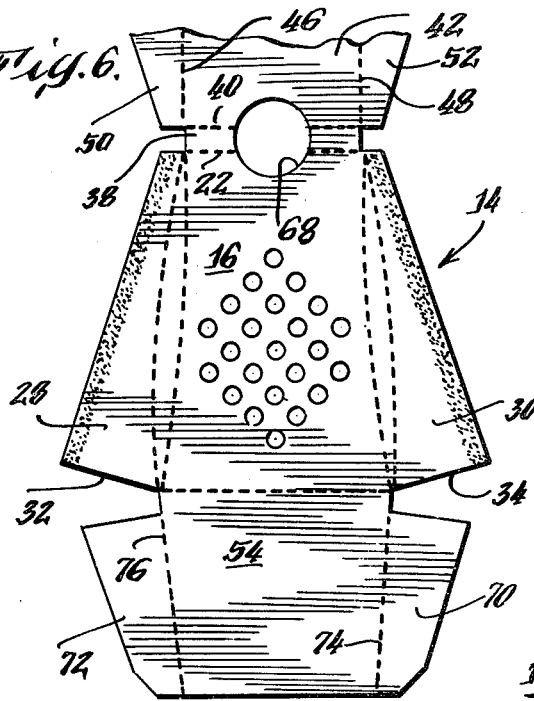
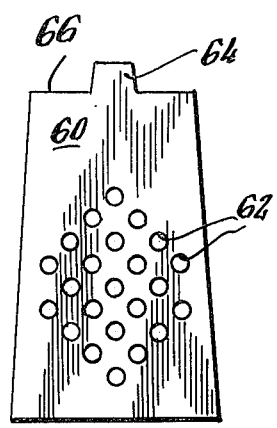
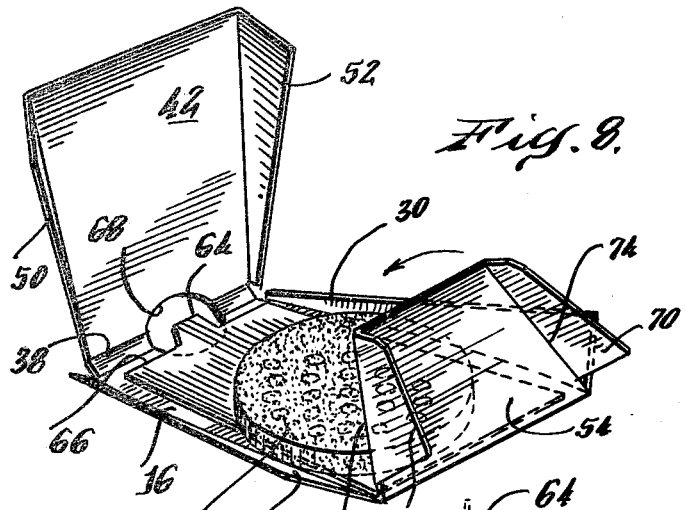
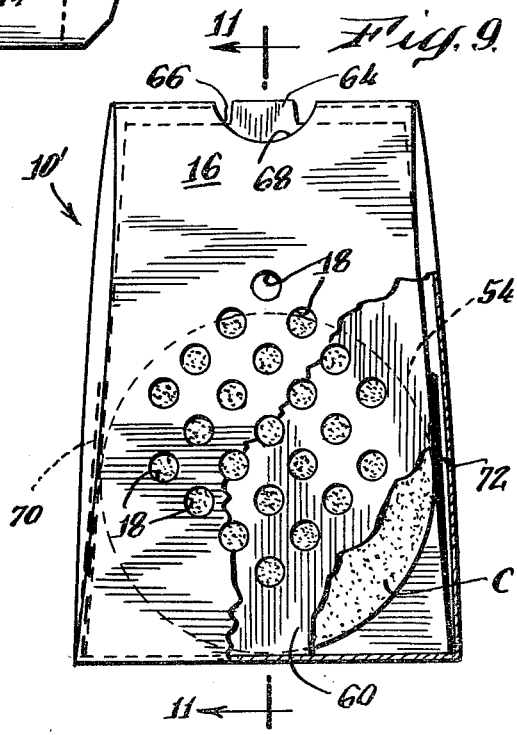
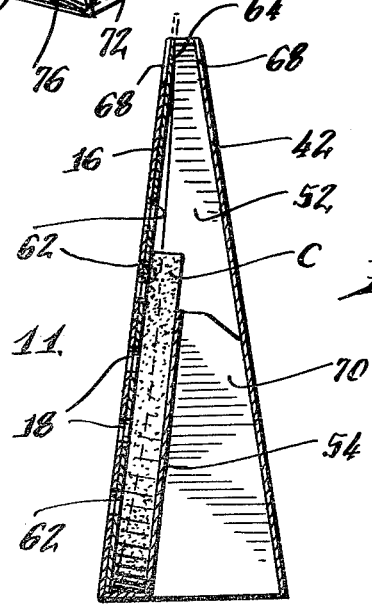
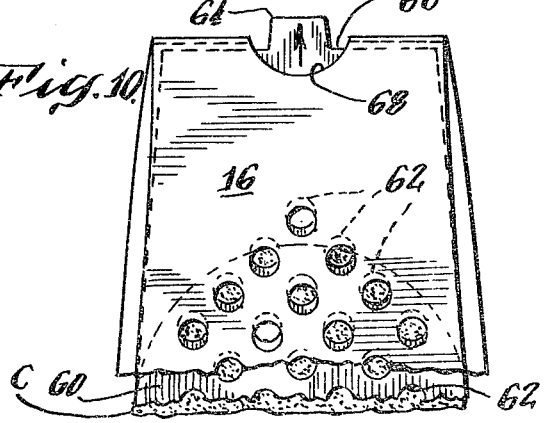

DIFFUSER CARTON

BACKGROUND OF THE INVENTION

1. Field of the Invention

The present invention relates to cartons and more particularly, to a carton for receiving and diffusing through openings formed therein an insert of solid air freshener material or the like.

2. Description of the Prior Art

Solid air fresheners are often sold in sealed outer containers having one or more openings in the container walls to permit room air to circulate past the air freshener material or the air freshener material to diffuse through the openings and mingle with the room air to freshen the same. The openings are normally covered by a panel of release paper until a consumer is ready to use the air freshener material. The panel is then stripped away to expose the openings and thus the surface of the solid air freshener within the container to room air.

Air freshener containers of molded plastic are known. Such molded plastic containers normally include a shell and a separate front piece which is affixed to the shell only after the solid air freshener has been loaded into place. While molded plastic shells may have an aesthetically pleasing appearance, the costs of manufacturing and using such molded plastic containers are high. The shell and front piece must be molded in separate operations and stored in unassembled form until the solid air freshener is loaded into place. Then, the front piece must be glued or otherwise secured to the shell to close the carton.

The extra time required to manufacture and assemble containers from the two separate molded plastic pieces increase manufacturing costs. Moreover, since the plastic shells must be shipped and stored in their molded, unassembled form, transportation and storage costs must also be incurred by the manufacturer.

SUMMARY OF THE INVENTION

The present invention is a one-piece carton which may be made from a low cost, foldable material such as paperboard and which may be shipped and stored in a flattened or collapsed condition until ready to be loaded with an insert of solid air freshener material or the like.

A blank for making such a carton includes a generally trapezoidal front and rear panel hingedly connected along their upper edges. The front and rear panels are also provided with generally triangular side flaps foldable relative thereto about vertical score lines. The score lines on the front panel may be spaced concave and convex lines so that when the blank is assembled, the front panel will include a relief portion along opposite edges so as to present an aesthetically pleasing appearance. Connected to the lower edge of the front panel is a closure flap.

In assembling the blank, the rear panel is folded relative to the front panel so that the panels are in spaced relation. The front panel is provided with a plurality of openings to serve as diffusing openings for the solid air freshening material to diffuse through and mingle with room air or alternatively, for room air to enter into contact with the solid air freshener material. A cake of such material is placed between the front and rear panels and then the closure panel connected to the bottom edge of the front panel is folded into the interior of the carton behind the cake to hold it adjacent the openings in the front panel. The triangular side flaps are overlapped and adhesively connected to maintain the components in assembled relation. A suitable release paper can be secured over the front panel to cover the openings until the air freshener material is ready to be diffused and the carton placed in use.

Alternatively, a slide may be positioned within the interior of the carton in front of the air freshener cake. The slide includes a plurality of openings adapted to be placed in and out of registration with the openings in the front panel of the carton. The slide can extend through an opening formed in the top wall connecting the front and back panels so that it can be grasped and slid relative to the openings in the front panel to uncover or cover the same depending upon whether the freshener carton is to be used.

BRIEF DESCRIPTION OF THE DRAWINGS

Further objects and advantages of the invention will become apparent from the following description and claims, and from the accompanying drawings, wherein:

FIG. 1 is a plan view of a blank used to form the diffuser carton of the present invention;

FIGS. 2 and 3 are perspective views of the blank of FIG. 1, partially folded to form the diffuser carton;

FIG. 4 is a perspective view of the diffuser carton of the present invention;

FIG. 5 is a cross-sectional view taken substantially along the plane indicated by line 5—5 of FIG. 4;

FIG. 6 is a plan view of an alternate form of a blank which can be used to form the diffuser carton of the present invention;

FIG. 7 is a plan view of a slide which is assembled with the blank of FIG. 6;

FIG. 8 is a perspective view of a partially folded and assembled blank and slide of FIGS. 6 and 7;

FIG. 9 is a front view in elevation, partially broken away, of a diffuser carton formed from the blank of FIG. 6 and slide of FIG. 7;

FIG. 10 is a partial front view in elevation, similar to FIG. 9, but illustrating the closure of the diffuser carton using the slide of FIG. 7; and FIG. 11 is a cross-sectional view taken substantially along the plane indicated by line 11—11 of FIG. 9.

DETAILED DESCRIPTION OF THE PREFERRED EMBODIMENT

Referring now to the drawings in detail, wherein like numerals indicate like elements throughout the several views, the diffuser carton of the present invention is formed from either the blank 12, as shown in FIG. 1, or the blank 14, as shown in FIG. 6.

Referring to FIG. 1, the blank 12 includes a generally trapezoidal front panel 16 provided with a plurality of openings 18 therethrough. The bottom edge 20 of front panel 16 is of a greater horizontal dimension than the top edge 22. The sides of front panel 16 are defined by concave score lines 24 and 26. Connected to the concave score lines 24 and 26 are side flaps 28 and 30, respectively.

The side flap 28 is generally triangular in shape and includes a bottom edge 32 disposed at an obtuse angle with respect to the bottom edge 20 of the front panel. Similarly, the other side flap 30 is generally triangular in shape and includes a bottom edge 34 disposed at an obtuse angle with respect to the bottom edge 20 of the front panel 16. A convex score line 36 is formed intermediate the outer edge of each side flap 28 and 30 and the adjacent concave score line 24 or 26 defining the lateral extent of the front panel 16. The score lines 36 extend from the juncture of the bottom edge of each of the side panels 28 and 30 with the bottom edge of the front panel 16 to the juncture of the top edge of the general triangular side flap 28 and 30 with the top edge 22 of the front panel 16. When a carton 10 is constructed (FIG. 4), the area between score lines 24 and 36 and 26 and 36 on each of the side flaps 28 and 30, respectively, will form a relief area or depression to increase the aesthetic appearance of the front of the carton 10.

Connected to the top edge 22 of front panel 16 is a generally rectangular panel 38. Panel 38 is connected to the top edge 22 of the front panel 16 by a score line running along top edge 22 and is connected by a parallel score line 40 to a rear panel 42 which is generally the mirror image of front panel 16.

Rear panel 42, being generally the mirror image of front panel 16 is generally trapezoidal in shape with its top edge 40 smaller in horizontal dimension than its bottom edge 44. The side eges of rear panel 42 are defined by straight score lines 46 and 48. Connected to the score line 46 is a generally triangular side flap 50, while connected to the score line 48 is a generally rectangular side flap 52 which is complimental in shape and dimension to the side flaps 28 and 30, respectively.

Connected to the bottom edge 20 of the front panel 16 by a score line is a trapezoidal vertical extension flap 54. Flap 54 is generally complimental in shape to the front and rear panels 16 and 42, respecitvley, and will fit therebetween when folded about the bottom edge 20 of the front panel 16.

In assembling the blank 12 into the carton configuration 10, rear panel 42 is first folded about the score lines 40 and 22 defining the top panel 38 so that is overlies in spaced relation front panel 16, as shown in FIGS. 2 and 3.

The triangular side flaps are then folded about score lines 46 and 48 and placed in alignment and in abutment with the side flaps 28 and 30 connected by the convex score lines 24 and 26, respectively, to the front panel 16. The interior surface of flap 28 is then adhesively secured to the exterior surface of flap 50, while the exterior surface of flap 30 is adhesively secured to the exterior surface of flap 52.

A solid cake of air freshener material C is then placed through the bottom of partially erected carton 10 into the interior thereof overlying openings 18 and front panel 16. Vertical, trapezoidal extension flap 54 is then folded about the score line contiguous with bottom edge 20 and disposed within the interior of carton 10 in back of the solid air freshener cake (see FIG. 5). Flap 54 holds the cake in abutment with the interior surface of the front panel 16 adjacent openings 18.

A suitable release paper may be placed over the openings 18 on the exterior surface of front panel 16 until the carton is ready for use in a room. At that time, the release paper is removed and air may enter the interior of the carton and flow past the cake. Alternatively, the solid material may diffuse and mingle with air through the openings 18.

Alternatively, a carton 10' may be formed from a blank 14, as shown in FIG. 6.

The blank 14 is substantially identical in construction to the blank 12 and similar elements are indicated by identical numerals as those found on blank 12. In addition, a planar slide 60 having openings 62 and a tab 64 connected to its upper edge 66 may be disposed within the interior of carton 10 between the air freshener cake C and the interior surface of the front panel 16. The openings 62 in the slide 60 are adapted to be placed in and out of registration with the openings 18 in the front panel 16. This is accomplished by providing a circular opening 68 in the top panel 38 and extending into a portion of the rear panel 42 and front panel 16. Tab 64 extends through opening 68 and the outer dimensions of slide 60 are also trapezoidal approximating very closely the dimensions of panel 16. Accordingly, by raising the slide slightly by pulling upwardly on tab 64, as shown in FIG. 10, the openings 62 and 18 will be taken out of registration to preclude diffusion of the air freshener cake until it is ready to be used. By sliding the tab 64 downwardly, as in FIG. 9, the opening 62 will be placed in registration with the openings 18 in the front panel 16 permitting diffusion and mingling of the air in a room with the air freshener cake through the registered openings.

The lower vertical flap 54 may be provided with substantially triangular side flaps 70 and 72 connected by score lines 74 and 76, respectively, to the lateral edges of flap 54. When flap 54 is inserted within the interior of the carton 10' to retain the air freshener cake in abutment with the rear of the slide 60, the side flaps 70 and 72 can be placed in frictional engagement with the flaps 50 and 52 of the rear panel to furnish lateral stability for the entire carton construction. As shown in FIG. 8, the preferred folding sequence of blank 14 may vary slightly from that utilized in connection with blank 12 in that the flap 54 is first placed in clamping engagement over cake C before sealing the triangular side flaps 28, 50 and 30, 52, facilitating the insertion of flap 54 into the interior of carton 10' because of the flaps 70 and 72.

What is claimed as new is:

1. A carton for receiving an insert comprising:
   a front panel having at least one opening therethrough,
   a solid rear panel substantially comprising the mirror image of said front panel, and
   a top panel hingedly connected between a top edge of each of said front and rear panels, with an opening formed in said top panel,
   said front and rear panels including
   a side flap hingedly connected to opposed lateral edges thereof, one of said side flaps of said front panel being complimentary shaped, overlapped, and secured to one of the side flaps of said rear panel, and the other of said side flaps of said front panel being complimentary shaped, overlapped, and secured to the other side flap of said rear panel, and
   a planar slide having at least one opening therethrough adapted to be placed in and out of registration with said opening in said front panel disposed within said carton between said overlapping side flaps and said front and rear panels, said slide including
   a pull tab connected to a top edge thereof recieved through the opening in said top panel, and
   a closure flap hingedly connected to a bottom edge of said front panel adapted to be inserted into said carton between said overlapped side flaps in spaced relation to said front panel to hold an insert in clamped relation to said front panel adjacent said opening therethrough.

2. The carton of claim 1 wherein said closure flap includes a side flap hingedly connected to opposed lateral edges thereof foldable into abutting relation with one of said overlapped pair of side flaps of said front and rear panels to rigidify said carton.

3. The carton of claim 1 wherein said front and rear panels are substantially trapezoidal in shape.

4. The carton of claim 3 wherein said side flaps of said front and rear panels are substantially triangular in shape and are connected to the lateral edges of its respective panel at an obtuse angle to the bottom edge thereof.

5. The carton of claim 4 wherein the lateral edges of said front panel are concave and the lateral edges of said rear panel are straight.

6. The carton of claim 5 wherein a convex score line is provided in each side flap connected to said front panel extending from one juncture of said side flap to said front panel to the other.

* * * * *